(12) United States Patent
Keller et al.

(10) Patent No.: US 12,398,082 B2
(45) Date of Patent: Aug. 26, 2025

(54) METHOD AND PLANT FOR PRODUCING ETHYLENE AND/OR OTHER OLEFINS BY STEAM CRACKING

(71) Applicants: LINDE GMBH, Pullach (DE); BASF SE, Ludwigshafen (DE)

(72) Inventors: Benedikt Keller, Munich (DE); Peter Brehm, Unterschleissheim (DE); Clemens Prunner, Neufarn (DE); Hendrik Reyneke, Munich (DE); Martin Kamann, Oberhaching (DE); Gunter Garbe, Rodenbach (DE); Daniel Keck, Ketsch (DE); Carl Schietekat, Sint-Niklaas (BE); Axel Sperber, Ludwigshafen (DE); Alexander Weck, Hochdorf-Assenheim (DE)

(73) Assignees: Linde GmbH, Pullach (DE); BASF SE, Ludwigshafen (DE)

( * ) Notice: Subject to any disclaimer, the term of this patent is extended or adjusted under 35 U.S.C. 154(b) by 99 days.

(21) Appl. No.: 18/546,459

(22) PCT Filed: Feb. 15, 2022

(86) PCT No.: PCT/EP2022/053626
§ 371 (c)(1),
(2) Date: Aug. 15, 2023

(87) PCT Pub. No.: WO2022/171894
PCT Pub. Date: Aug. 18, 2022

(65) Prior Publication Data
US 2024/0239728 A1    Jul. 18, 2024

(30) Foreign Application Priority Data
Feb. 15, 2021   (EP) .................................... 21157138

(51) Int. Cl.
*C07C 4/04*     (2006.01)
*B01J 3/04*     (2006.01)
(Continued)

(52) U.S. Cl.
CPC ................... *C07C 4/04* (2013.01); *B01J 3/04* (2013.01); *C10G 9/36* (2013.01); *F25J 3/06* (2013.01)

(58) Field of Classification Search
CPC ... B01J 3/04; C07C 4/04; C10G 9/002; C10G 9/36; C10G 70/04; C10G 9/00;
(Continued)

(56) References Cited

FOREIGN PATENT DOCUMENTS

EP       3730592 A1 *  10/2020

OTHER PUBLICATIONS

EP3730592 (Year: 2019).*
International Search Report and Written Opinion issued in related App. No. PCT/EP2022/053626 mailed Apr. 13, 2022.

* cited by examiner

*Primary Examiner* — Sharon Pregler
(74) *Attorney, Agent, or Firm* — Avek IP, LLC (57) ABSTRACT

A method for producing ethylene and/or other olefins by steam cracking includes charging one or more crackers with a paraffin-containing feed and withdrawing a crude gas from the one or more crackers. The crude gas is subjected at least in part to a treatment comprising a crude gas compression and a thermal separation using a C2 refrigerant and a C3 refrigerant. A crude gas compressor is used for the crude gas compression, wherein the ethylene refrigerant is compressed using a C2 refrigerant compressor. The propylene refrigerant is compressed using a C3 refrigerant compressor. The crude gas compressor comprises two serial compressor trains. The compressor trains, the C2 refrigerant compressor and the C3 refrigerant compressor are each operated at least in part (Continued)

using electrical drives, which have at least partially identical power features, are provided as variable-speed drives of the same construction, and are each fed via frequency converters.

18 Claims, 3 Drawing Sheets

(51) Int. Cl.
  *C10G 9/36* (2006.01)
  *F25J 3/06* (2006.01)
(58) Field of Classification Search
  CPC .......... F01K 23/06; F04D 25/04; F04D 25/06;
   F25J 3/0219; F25J 3/0238; F25J 3/0252;
   F25J 3/06; F25J 3/02
  See application file for complete search history.

METHOD AND PLANT FOR PRODUCING ETHYLENE AND/OR OTHER OLEFINS BY STEAM CRACKING

CROSS-REFERENCE TO RELATED APPLICATIONS

This application is the national phase of, and claims priority to, International Application No. PCT/EP2022/053626, filed 15 Feb. 2022, which claims priority to European Patent Application No. EP 21157138.5 filed 15 Feb. 2021.

FIELD OF THE INVENTION

The invention relates to a method and a plant for producing ethylene and/or other olefins by steam cracking.

BACKGROUND

Methods and plants for the steam cracking of hydrocarbons are described, for example, in the article "Ethylene" in Ullmann's Encyclopedia of Industrial Chemistry, online April edition, 15, 2009, DOI 10.1002/14356007.a10_045.pub2. Steam cracking is predominantly used to obtain short-chain olefins, such as ethylene and propylene, diolefins, such as butadiene, or aromatics, but is not limited to obtaining such compounds.

In steam cracking, component mixtures (also referred to as cracked gases or crude gases) are obtained which are subjected to suitable processing sequences in order to obtain the desired individual components. Typically, in a first section (front-end section) of a corresponding treatment sequence, heavy compounds are removed, if present, and then a so-called crude gas compression, acid gas removal and drying take place. The processing in the front-end section is followed by a fractionation in which fractions are formed by thermal separation processes using ethylene or C2 refrigerants and propylene or C4 refrigerants and are separated further if necessary. For details, reference is made to the cited article "Ethylene" in Ullmann's Encyclopedia of Industrial Chemistry, in particular sections 5.3.2.1, "Front-End Section", and 5.3.2.2, "Hydrocarbon Fractionation Section."

In one embodiment of a corresponding fractionation, which can also be used in the context of the present invention, the fractionation firstly involves separating hydrocarbons having two carbon atoms and lower boiling components, such as methane and hydrogen, from hydrocarbons having three carbon atoms and higher boiling compounds. Such a step is usually also referred to as deethanization, the configuration of a corresponding fractionation is referred to as a "deethanizer first" or "front-end deethanizer" method.

The fraction of hydrocarbons having two carbon atoms and lower boiling components obtained in gaseous form in the deethanization can be fed to a further separation in which the hydrocarbons having two carbon atoms are separated from the lower-boiling components also contained. Such a step is also referred to as demethanization. In a "deethanizer first" or "front-end deethanizer" method, the demethanization is therefore downstream of the deethanization.

In alternative methods, the steps of deethanization and demethanization can also be carried out in reverse order. This is then referred to as a "deethanizer first" or "front-end demethanizer" method. Further method variants are described in the cited technical literature.

Compressors are used at different locations as part of corresponding processing sequences. In particular, the crude gas compression is carried out using a cracked gas compressor (CGC), and a so-called ethylene refrigerant compressor (ERC) and a so-called propylene refrigerant compressor (ERC) are used in the provision of the ethylene or C2 refrigerants and the propylene or C3 refrigerants. These terms are used in the following, although optionally ethane can also be compressed in an ethylene refrigerant compressor and optionally propane in a propylene refrigerant compressor. Product fractions of the thermal separation can be subjected to compression using further compressors, so-called product compressors.

EP 3 730 592 A1 describes an olefin synthesis plant. This comprises a feed pretreatment section, configured to pretreat a feed stream, and a pyrolysis section comprising one or more pyrolysis reactors configured to crack hydrocarbons in the input stream in the presence of a diluent to produce a cracked gas stream. A primary fractionation and compression section is provided that is configured to provide heat recovery from the cracked gas stream and quenching of the cracked gas stream, remove a component from the cracked gas stream, and compress the cracked gas stream, thereby providing a compressed cracked gas stream. Alternatively or additionally, a product separation section may be provided which is configured to separate a product olefin stream from the compressed cracked gas stream. The olefin synthesis plant is configured such that, compared to a conventional olefin synthesis plant, a greater portion of the energy and/or the net energy required by the olefin synthesis plant and/or one or more portions thereof is provided by a non-carbon based and/or renewable energy source and/or electricity.

SUMMARY

According to one embodiment of the invention, a method for producing ethylene and/or other olefins by steam cracking, includes charging one or more crackers with a paraffin-containing feed, withdrawing a crude gas from the one or more crackers; and subjecting the crude gas at least in part to a processing comprising a crude gas compression and a thermal separation using a C2 refrigerant and a C3 refrigerant. A crude gas compressor is used for the crude gas compression. The C2 refrigerant is compressed using a C2 refrigerant compressor. The C3 refrigerant is compressed using a C3 refrigerant compressor. The crude gas compressor comprises two serial compressor trains. In each of these compressor trains, the C2 refrigerant compressor and the C3 refrigerant compressor are each operated at least in part using electrical drives, which have at least partially identical power features, are each powered via frequency converters, and are each provided as variable-speed drives of the same construction. Each of the serial compressor trains of the crude gas compression, the C2 refrigerant compressor, and the C3 refrigerant compressor are aligned with each other regarding their torque.

According to another embodiment of the invention, a plant for producing ethylene and/or other olefins by steam cracking includes one or more crackers configured for charging with a paraffin-containing feed and for producing a crude gas; a crude gas compressor comprising two serial compressor trains; a C2 refrigerant compressor; a C3 refrigerant compressor; and a plurality of electrical drives. Each of the plurality of electrical drives has at least partially identical power features. Each electrical drive is fed via frequency converters; and each of the plurality of electrical drives is of the same construction and is a variable-speed drive. The plant is configured to subject the crude gas at least in part to a treatment comprising a compression via the crude gas compressor, a thermal separation using a C2 refrigerant via the C2 refrigerant compressor, and a thermal separation using a C3 refrigerant via the C3 refrigerant compressor. At least a portion of the drive power of the two compressor trains of the crude gas compressor, of the C2 refrigerant compressor, and of the C3 refrigerant compressor is provided by respective electrical drives of the plurality of electrical drives. Each of the serial compressor trains of the crude gas compression, the C2 refrigerant compressor, and the C3 refrigerant compressor are matched to one another in terms of their torque.

DETAILED DESCRIPTION

An object of the invention is to improve corresponding methods and plants and, in particular, also to configure them to be adaptable to the respective energy range at plant site. This and other objects are achieved by a method and a plant for producing ethylene and/or other olefins by steam cracking.

Overall, the invention proposes a method for the production of ethylene and/or other olefins by steam cracking, in which one or more crackers, i.e., cracking furnaces, which can be embodied in the usual manner with a convection and radiation zone, are charged with a paraffin-containing feed, such as naphtha or ethane or corresponding mixtures or any other feeds known or advantageous in the art, and in which a crude gas is withdrawn from the one or more crackers, wherein the crude gas is subjected at least in part to a processing which comprises a crude gas compression and a thermal separation using an ethane and/or ethylene refrigerant (C2 refrigerant) and a propane and/or propylene refrigerant (C3 refrigerant). The refrigerants mentioned can be used in particular for condensing gas mixtures, for bringing sump evaporators of separation columns to the boil or in corresponding head condensers.

Where an "ethane and/or ethylene refrigerant" or "C2 refrigerant" or a "propane and/or propylene refrigerant" or "C3 refrigerant" is mentioned here, they may be corresponding pure substances or mixtures of the components mentioned. In each case, other components may also be contained, typically in smaller amounts of less than 10%.

A crude gas compressor is used within the scope of the invention to compress the crude gas, the C2 refrigerant is compressed using a C2 refrigerant compressor, and the C3 refrigerant is compressed using a C3 refrigerant compressor. For further details of a corresponding method, which will also be explained by way of example below, reference is expressly made to the prior art cited at the outset. As mentioned, the C2 refrigerant compressor and the C3 refrigerant compressor are also referred to in simplified form as the C2 refrigerant compressor (ERC) or C3 refrigerant compressor (PRC).

According to the invention, the crude gas compressor has two serial compressor trains, and each of these compressor trains, the C2 refrigerant compressor and the C3 refrigerant compressor are operated in each case at least in part using electrical drives. To avoid misunderstandings, it is pointed out that the statement that certain compressors or compressor trains are "each" driven using electric drives is to be understood such that one of the compressor trains is driven by a first of the electric drives, the other compressor train is driven by a second of the electric drives, the C2 refrigerant compressor is driven by a third of the electric drives and the C3 refrigerant compressor is driven by a fourth of the electric drives. In the context of the invention, one of the compressor trains of the crude gas compressor, in particular the upstream compressor train, comprises in particular two compressor stages, the other compressor train in particular three. More generally, the compressor trains comprise in particular a different number of compressor stages. As has been recognized according to the invention, the mode of operation proposed according to the invention offers particular advantages over drives known from the prior art, for example by means of condensation steam turbines according to API 612 or others. In such a conventional mode of operation, the following description of which is not intended to limit the invention in any way, the crackers are provided, for example, with the use of waste heat, the cracker is provided with ultrahigh-pressure steam (HHP steam), i.e., steam at a pressure level of 90 to 130 bar and a temperature level of 450 to 540° C. and is used to drive the crude gas compressor. The ultrahigh-pressure steam is typically expanded via a high-pressure section of the drive turbine of the crude gas compressor. A significant portion of the steam is subsequently extracted as high-pressure steam (HP steam), i.e., steam at a pressure level of 35 to 50 bar and a temperature level of 250 to 400° C. and supplied to the drive turbines of the C2 refrigerant compressor and the C3 refrigerant compressor. Depending on the requirement of further consumers, medium-pressure steam (MP steam) or low-pressure steam (LP vapor), i.e., steam at a pressure level of 15 to 25 bar and a temperature level of 200 to 250° C. or steam at a pressure level of 3 to 8 bar and a temperature level of 150 to 190° C. are also produced. To raise the total energy balance, additional steam can be imported from high-pressure steam generators or imported from external sources. Steam export for balancing can also be provided via the plant boundary in this case.

The energy balancing of the conventional method just described must take place taking into account the restrictions resulting from the power demand of the three large consumers, i.e., the crude gas compressor, the C2 refrigerant compressor and the C3 refrigerant compressor. This usually requires the installation of a high-pressure steam generator comprising a corresponding steam boiler in order to release the coupling of ultrahigh-pressure and high-pressure steam requirements for the energy balancing. This increases the structural complexity. In addition, the condensation heat of the steam remains largely unused, whilst instead the waste steam from the turbines is typically condensed by means of cooling water with a high outlay in terms of apparatus. Ultrahigh-pressure and high-pressure steam generators are associated with considerable carbon dioxide emissions; an integration of alternative (optionally carbon dioxide neutral) energy to drive the compressors is usually not provided or possible.

The use of the invention results in a flexibilization of the ethylene production or the production of other olefins with respect to steam and carbon dioxide balancing due to the very much greater independence during operation of the compressors resulting from the use of the electric drives. In particular, the rigid coupling of the high pressure steam utilization in the crude gas compression and the subsequent use of high-pressure steam in the compression of the refrigerant no longer presents an obstacle to flexibilization in the context of the present invention.

According to a particularly preferred embodiment of the invention, ultrahigh-pressure steam is still provided using waste heat from the cracker or the crackers. However, this is advantageously exported at least in part from the plant and/or is used at least in part as a heat source for other method steps, without being used for driving the crude gas compressor, the C2 refrigerant compressor and the C3 refrigerant compressor.

In a particularly preferred embodiment of the invention or as an alternative to the measures proposed according to the invention, the ultrahigh-pressure steam can be adapted in terms of pressure and/or temperature for the aforementioned export and/or the intended use in an adaptation unit, a so-called let-down station. In the adaptation unit, it is also possible, in particular, to use any condensation heat arising for other purposes, for example for feeding into a district heating network.

According to a particularly preferred embodiment, the method used according to the invention can be carried out without using a high-pressure steam boiler. In other words, the use of the invention allows a corresponding high-pressure steam boiler to be omitted so that the demand for fossil energy carriers is reduced and the carbon dioxide balance is thus improved. In principle, in the context of the invention, it is possible to incorporate carbon dioxide-neutral energy at any point, resulting in considerable flexibilization with respect to the carbon dioxide footprint. As mentioned, the crude gas compressor according to the invention comprises two serial compressor trains, i.e., individually drivable structural units, wherein each of the compressor trains of the crude gas compressor and the C2 refrigerant compressor and the C3 refrigerant compressor are each operated by means of electrical drives having at least partially identical power features. Advantageously, the drives can also be substantially of the same construction. In this way, the number of common parts increases and the creation of a corresponding plant is significantly improved within the meaning of a standardization concept.

The electrical drives having at least partially identical power features are provided as variable-speed drives of the same construction and these are each supplied via frequency converters. Each of the serial compressor trains of the crude gas compression, the C2 refrigerant compressor and the refrigerant compressor are adapted to one another in terms of their torque. In this way, a corresponding standardization with simultaneous flexibility in the rotational speed can be achieved. In particular, four frequency converters can be provided here, of which two or even all four can be used for feeding the electric drives at any point in time that the plant is in operation. A fifth frequency converter can be kept ready for redundancy reasons, in particular for necessary maintenance and/or repair work.

The use of the invention makes it possible to fall back on machines of the same construction, in particular, for the drives, so that in particular the warehousing of the (common) parts required for these machines and the maintenance are simplified. The invention is based on the knowledge that the use of drives of the same construction is nevertheless possible and advantageous in spite of the difficulties associated therewith and corresponding concerns among experts. The invention thus particularly achieves an improvement in the creation and operation of corresponding plants, wherein the measures proposed according to the invention or according to embodiments of the invention were not obvious from the prior art.

The alignment of the performance of the drives is not trivial since crude gas compressors, ethylene and propylene compressors exhibit considerably different performances. Furthermore, the ratio of the performance of ethylene compressor and propylene compressor is variable, specifically as a function of feed and process management (separation of heavier hydrocarbons, in particular having five or more carbon atoms. The crude gas compressor typically comprises five stages, which speaks prima facie against divisibility. The pressure conditions at the crude gas compressor can only be shifted to a limited extent since high pressure conditions in the individual stages could lead to high temperatures and thus to the risk of fouling. Without knowledge of the embodiments of the invention, this would have stopped the person skilled in the art from taking a corresponding solution into consideration.

In the context of embodiments of the invention, in particular the crude gas compressor can be divided into two and three stages in the manner explained above and a displacement of the pressure conditions within the scope of the given limitations, moreover, in particular, a use of external refrigeration, can also take place, as is provided according to an embodiment of the invention. This in turn also leads to a desired loading of a propylene compressor, used in particular thereby, and therefore to the alignment of propylene and ethylene compressor.

The use of variable-speed drives of the same construction is also not obvious without knowledge of the invention or corresponding embodiments of the invention, because not only the power but the torque even more so must be aligned. This means that the compressors either rotate at a similar speed or gear mechanisms have to be used (conversion of speed and torque). Without aligning the torque, the motors cannot be standardized, even at the same power. Therefore, in the present case in particular one or more gear mechanisms are used.

Advantages of embodiments of the invention result in particular from the provision of a redundancy n+1 with the use of an additional frequency converter. In other embodiments of the invention, this can also be achieved with different frequency converters and/or drives, but while accepting corresponding adjustments in terms of efficiency, spare parts inventory and dimensioning. The additional frequency converter must correspond here to the largest of the four regularly used frequency converters and, without load alignment, this would inevitably be greater than the average power in the case of four identical drives.

The four frequency converters can be installed in pairs with complete redundancy (2×100%), wherein the two frequency converters of each pair can be operated in partial load operation (2×50%) in parallel or in switching mode (alternately) with full load (1×100% in each case). In the case of two independent supply networks, the frequency converters can advantageously be connected to the two networks. This redundancy concept is particularly suitable if voltage drops/failures in the supply networks are expected and switching times to increase plant availability are to be minimized.

For powerful drives beyond the performance limit of a frequency converter, a 3×50% redundancy concept is also conceivable, in which two frequency converters operated in parallel provide the total power of 100%.

In one embodiment of the method according to the invention, the four frequency converters and the fifth frequency converter are each provided as part of a frequency converter arrangement, wherein the frequency converter arrangement of the fifth frequency converter is held in operative state during the execution of the method, in particular in a hot standby state, i.e., in the at least partially energized state, which is explained below.

According to one embodiment, the frequency converter arrangements each comprise an input transformer, in particular a VSD transformer and an input and output, wherein the input and output (the input, in particular via the input transformer) are connected to a current source and the respective drive by means of switching units. By selective activation of the switching units at the output, the respective frequency converter can be selectively connected to the drive instead of another.

Variable-speed electric drives according to the current standard have an average operating time until failure or between repairs (mean time between failures MTBF or to repair, MTTR) of about 10 years. Since, however, all three compressors (CGC, ERC and PRC) are required at the same time for plant operation, the availability is reduced (for example, by means of a reliability block diagram) so that an industry standard uninterrupted plant operation of 5 years is difficult to realize. However, the standardization of the drives makes it possible main spare parts, which are sometimes necessary anyway, to be installed in "cold standby" or "hot standby." Therefore, in the event of a failure, it is advantageously possible to switch over between corresponding units without (significant) delay. As a result, the MTBF or MTTR can be increased in the context of the invention, for example to up to 20 years.

In the embodiment of the invention explained, a fifth frequency converter, advantageously including peripheral devices (cooling, transformer, switching devices), is therefore installed ready for use and interconnected in such a way that it can be used as a redundancy for each of the four existing frequency converters. A temporary shutdown of the machine or standstill can be considered ("cold standby") for the switchover. Alternatively, a switchover can be performed during operation, wherein the interruption of the drive torque is to be minimized. Switching times of less than 500 ms are technically possible and desirable; in terms of control technology, the switchover sequence is optionally to be coupled to the pump protection control of the compressors (feed forward signal to the anti-surge controller).

In the embodiment of the invention, corresponding transformers and frequency converters are in particular so-called "capital spare parts," i.e., they are already provided during the installation of a corresponding plant and are continuously held ready during operation. They are thus included in the investment costs.

If these spare parts are not taken into the warehouse, as is provided in embodiments of the invention, but are instead provided as "installed" spare parts, they are ready for use in a very short time, for example within the aforementioned 500 ms.

A particular advantage of the invention is also that the crude gas compressor, the C2 refrigerant compressor and the C3 refrigerant compressor can be set up at ground level, since capacitors that require table foundations are not necessary.

Advantageously, an intermediate cooling can be carried out in the crude gas compressor at least temporarily using external refrigeration, for example by using propane or propylene cold (C3 refrigeration). In principle, this intermediate cooling can take place before each stage. Pre-cooling, in particular of the fourth stage, is particularly favorable since as a result the same performance of the first to third stages on the one hand and of the fourth and fifth stages on the other hand can be achieved, while avoiding impermissibly high exit temperatures. In this context, a different distribution of compressor stages to drives can be provided than was explained above in an example. This is particularly advantageous within the meaning of the described standardization. In the context of the invention, the external refrigeration for the intermediate cooling can be provided using at least a portion of the C2 refrigerant and/or the C3 refrigerant, in that corresponding refrigerant is coupled out of the respective refrigerant circuits.

In embodiments of the invention, the aforementioned intermediate cooling can be carried out either permanently or, using external refrigeration, (only) when a cooling water temperature and/or water injection is recognized as being insufficient and/or not functional. This makes it possible to optimize operating costs.

In the context of the invention, provision is made in a particularly preferred embodiment for the drive powers of the electric drives of the crude gas compressor, the C2 refrigerant compressor and the C3 refrigerant compressor to be adjusted by a displacement of cooling power between a C2 refrigerant circuit in which the C2 refrigerant is used and a C3 refrigerant circuit in which the C3 refrigerant is used and/or by the explained integration of C3 refrigeration as additional intermediate cooling of the crude gas compressor in order to homogenize the power requirement as much as possible.

The invention also extends to a plant for the production of ethylene and/or other olefins by steam cracking, having one or more crackers which are configured to charge with a paraffin-containing feed and to provide a crude gas, wherein the plant is configured to subject the crude gas at least in part to a processing which comprises crude gas compression and thermal separation using a C2 refrigerant and a C3 refrigerant, wherein a crude gas compressor is provided for the crude gas compression, a C2 refrigerant compressor is provided for compressing the C2 refrigerant, and a C3 refrigerant compressor is provided for compressing the C3 refrigerant. Regarding the features according to the invention, reference is made to the corresponding independent claim.

For features and advantages of a corresponding plant and advantageous embodiments thereof, reference is expressly made to the above explanations regarding the method proposed according to the invention and its embodiments, since these also apply in a corresponding manner to the plant and to the embodiments thereof. This is, in particular, also the case in a plant which is designed to carry out a method, as has been explained above in different embodiments.

The invention is described in more detail below with reference to the accompanying drawings, which illustrate embodiments of the invention.

Figure 1:
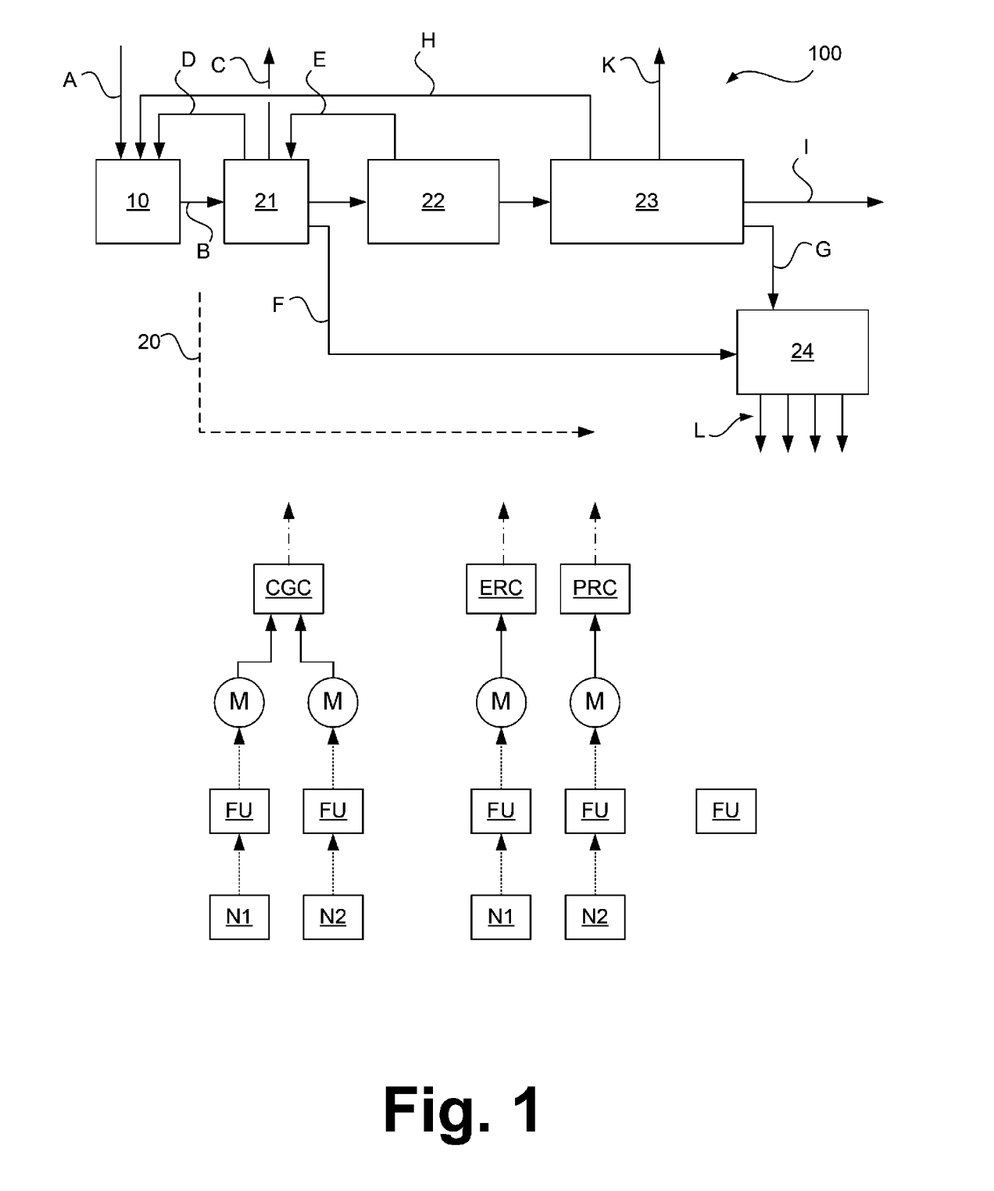
FIG. 1 is a simplified process flow diagram according to an embodiment of the invention.

In FIG. 1, a method according to an embodiment of the invention is illustrated in the form of a simplified process flow diagram and is denoted as a whole by 100. Although the following explanations relate to a method and corresponding method steps, they apply to a corresponding plant and its components in the same way.

In the method 100, one or more crackers (cracking furnaces) 10 are used, which are charged with a feed A (as well as steam, as not illustrated separately here) and from which a crude gas B is withdrawn.

The crude gas B is subjected at least in part to a treatment designated here as a whole by 20, which in a manner known per se comprises a quenching step 21 with separation of pyrolysis oil C and a compression (crude gas compression) 22 and a thermal separation 23 using a C2 refrigerant and a C3 refrigerant. In the quenching step 21, steam D can be provided and recycled into the cracker or crackers 10. In the compression 22, pyrolysis gasoline E can be separated off and recycled into the quenching step 21, for example. In the quenching step 21, hydrocarbons F having three or more carbon atoms can be separated off further and transferred into a corresponding processing step 24, in which corresponding hydrocarbons G can also be fed from the thermal separation 23. In the thermal separation 23, an ethane stream H can be provided and recycled into the cracking furnace or cracking furnaces 10. An ethylene stream I can be realized as a product. So-called tail gas K, which contains in particular methane and hydrogen, is discharged. Further product flows, denoted overall by L, are provided in the further processing step 24.

As illustrated symbolically in a lower region of FIG. 1, a compressor denoted by CGC is used for the crude gas compression 22, and the ethylene refrigerant is compressed using a C2 refrigerant compressor denoted by ERC, and the propylene refrigerant is compressed using a C3 refrigerant compressor denoted by PRC. The crude gas compressor CGC, the C2 refrigerant compressor ERC and the C3 refrigerant compressor PRC are each operated at least in part using one or more electric drives M.

More precisely, in the embodiment of the invention illustrated here, the crude gas compressor CGC comprises two serial compressor trains (not shown separately), wherein each of the compressor trains of the crude gas compressor CGC and the C2 refrigerant compressor ERC and the C3 refrigerant compressor PRC are operated in each case by means of electrical drives having at least in part identical power features. Said electrical drives can be provided here as variable-speed drives of the same construction and can each be fed via a frequency converter FU. Overall, in the example illustrated here, five frequency converters FU are provided, of which two (in paired full-load alternating operation) or four (in paired partial load operation) are used at any time to feed the electric drives M and one is kept ready for redundancy reasons. In the example illustrated here, the frequency converters FU are connected to different networks or power supplies N1, N2 in the manner shown. The invention is not limited by the example illustrated here.

The steam D or other steam provided in the method can comprise in particular ultrahigh-pressure steam which is exported and/or is used least in part as a heat source for other method steps, without being used to drive the crude gas compressor RGC, the C2 refrigerant compressor ERC and the C3 refrigerant compressor PRC. In terms of pressure and/or temperature for export and/or intended use, the ultrahigh-pressure steam can be adapted to an adaptation unit indicated here generally with 50. Condensation heat accumulating in the adaptation unit 50 can be used in the manner explained.

For further embodiments of the invention, all of which can also be used in the method 100 shown in FIG. 1, reference is again made explicitly to the above explanations.

Figure 2:
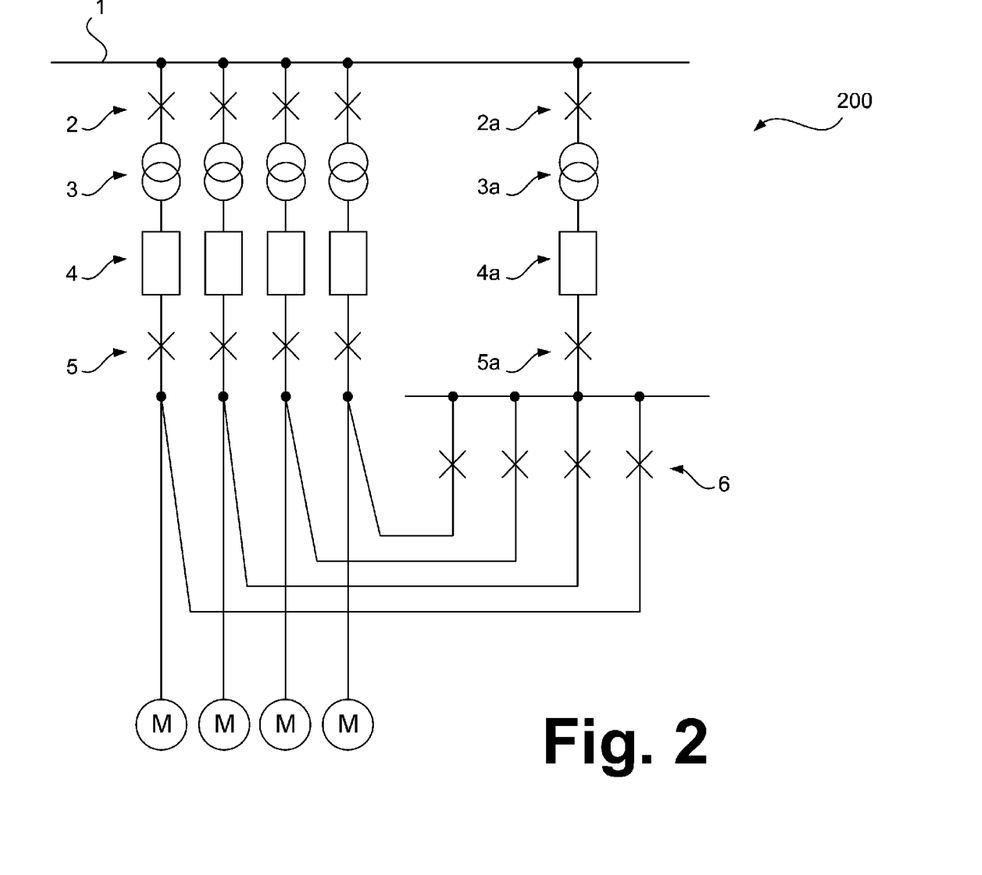
FIG. 2 illustrates an arrangement according to an embodiment of the invention.

FIG. 2 illustrates an arrangement 200 according to an embodiment of the invention. A plurality of preferably identical elements are illustrated in each case and are therefore only provided with corresponding reference signs once in each case.

Input transformers (in particular VSD transformers) are connected to a bus bar 1 via switching devices 2, each input transformer being embodied by frequency converters, denoted here by 4, and in particular as indirect converters with DC voltage in the intermediate circuit (VSI). The respective drives are again connected via switching devices 5. The group of switching devices 2a and 5a shown in the figure and input transformer 3a and frequency converter 4a can be selectively connected to one of the drives M by means of one of the switching devices 6 when the drive M has been separated from the originally connected frequency converter via the corresponding switching device 5. The switching device 2a can remain closed throughout the operation, so that the input transformer 3a and frequency converter 4a can be kept in "hot standby."

Figure 3:
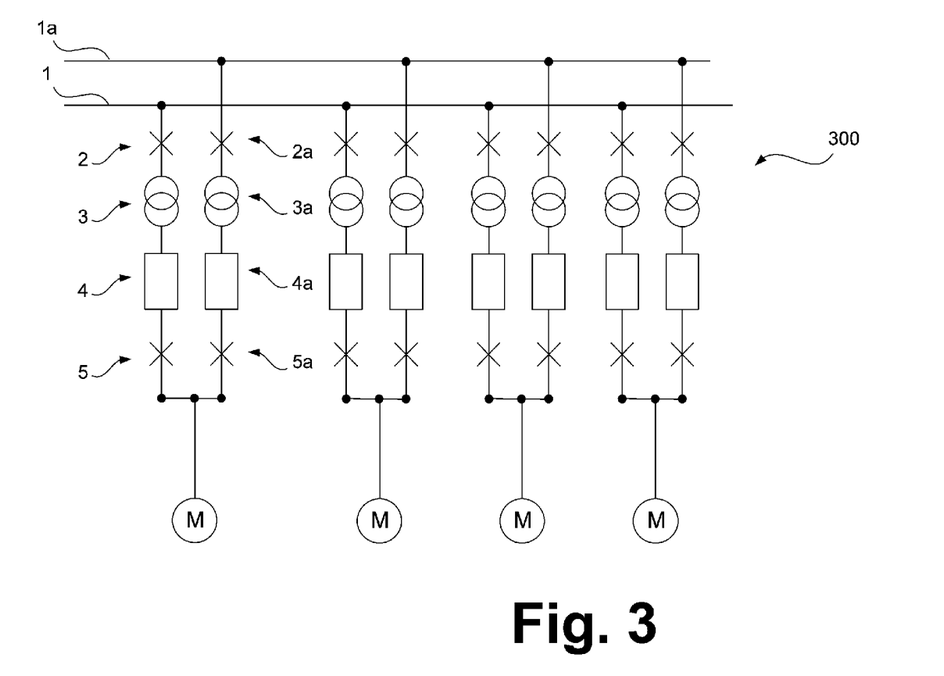
FIG. 3 illustrates another arrangement according to an embodiment of the invention.

FIG. 3 shows an arrangement 300 according to a further embodiment of the invention. Here too, in each case a plurality of preferably identical elements are illustrated, which are therefore only provided with corresponding reference numerals once in each case.

In contrast to the arrangement 200 illustrated in FIG. 2, a different redundancy concept is shown in the arrangement 300 illustrated in FIG. 3, in which each of the drives M can alternatively be connected to one of two trains of switching devices 2 and 5, input transformer 3 and frequency converter 4 (or 2a, 5a, 3a, and 4a, only denoted accordingly on the left drive M).

The invention claimed is:

1. A method for producing ethylene and/or other olefins by steam cracking, comprising:
   charging one or more crackers with a paraffin-containing feed;
   withdrawing a crude gas from the one or more crackers; and
   subjecting the crude gas at least in part to a processing comprising a crude gas compression and a thermal separation using a C2 refrigerant and a C3 refrigerant, wherein:
      a crude gas compressor is used for the crude gas compression;
      the C2 refrigerant is compressed using a C2 refrigerant compressor; and
      the C3 refrigerant is compressed using a C3 refrigerant compressor;
   wherein:
      the crude gas compressor comprises two serial compressor trains;
      in each of these compressor trains, the C2 refrigerant compressor and the C3 refrigerant compressor are each operated at least in part using electrical drives, which have at least partially identical power features, are each powered via frequency converters, and are each provided as variable-speed drives having the same construction; and
      each of the serial compressor trains of the crude gas compression, the C2 refrigerant compressor and the C3 refrigerant compressor are aligned with each other regarding their torque.

2. The method according to claim 1, wherein, using waste heat from the one or more crackers, ultrahigh-pressure steam at a pressure level of 90 to 130 bar and a temperature level of 450 to 540° C. is provided and exported and/or used at least in part as heat source, without being used to drive the crude gas compressor, the C2 refrigerant compressor, and the C3 refrigerant compressor.

3. The method according to claim 2, wherein the ultrahigh-pressure steam is adapted in an adaptation unit with respect to pressure and/or temperature.

4. The method according to claim 3, which is operated without using a high-pressure steam boiler.

5. The method according to claim 1, wherein five frequency converters are provided, of which two or four are used at any time to feed the electric drives, and the fifth frequency converter is kept ready for necessary maintenance and/or repair work on one or more of the frequency converters feeding the electric drives, whereby the fifth frequency converter replaces the frequency converter in need of maintenance and/or repair work and thereby feeds the electric drives.

6. The method according to claim 5, wherein the four frequency converters and the fifth frequency converter are each provided as part of a frequency converter arrangement, wherein the fifth frequency converter with its frequency converter arrangement is held in operational state.

7. The method according to claim 6, wherein the frequency converter arrangements each comprise an input transformer and an input and output, wherein the input and output are connected via switching units to a current source and the respective drive.

8. The method according to claim 1, wherein the crude gas compressor, the C2 refrigerant compressor, and the C3 refrigerant compressor are set up at ground level.

9. The method according to claim 1, further comprising carrying out an intermediate cooling in the crude gas compressor at least temporarily using external refrigeration.

10. The method according to claim 9, wherein the external refrigeration is provided for the intermediate cooling using at least a portion of the C2 refrigerant and/or the C3 refrigerant.

11. The method according to claim 10, wherein the intermediate cooling is carried out using external refrigeration when a cooling water temperature and/or water injection is recognized as being insufficient and/or not functional.

12. The method according to claim 1, wherein drive powers of the electric drives of the crude gas compressor, the C2 refrigerant compressor, and the C3 refrigerant compressor are adjusted by a displacement of cooling power between an ethylene refrigerant circuit, in which the ethylene refrigerant is used, and a propylene refrigerant circuit, in which the propylene refrigerant is used and/or the integration of propylene refrigeration as additional intermediate cooling of the crude gas compressor.

13. A plant for producing ethylene and/or other olefins by steam cracking, comprising:
   one or more crackers configured for charging with a paraffin-containing feed and for producing a crude gas;
   a crude gas compressor comprising two serial compressor trains;
   a C2 refrigerant compressor;
   a C3 refrigerant compressor; and
   a plurality of electrical drives, wherein:
      each of the plurality of electrical drives has at least partially identical power features;
      each electrical drive is fed via frequency converters; and
      each of the plurality of electrical drives is of the same construction and is a variable-speed drive;
   wherein:
      the plant is configured to subject the crude gas at least in part to a treatment comprising a compression via the crude gas compressor, a thermal separation using a C2 refrigerant via the C2 refrigerant compressor, and a thermal separation using a C3 refrigerant via the C3 refrigerant compressor;
      at least a portion of the drive power of the two compressor trains of the crude gas compressor, of the C2 refrigerant compressor, and of the C3 refrigerant compressor is provided by respective electrical drives of the plurality of electrical drives; and
      each of the serial compressor trains of the crude gas compression, the C2 refrigerant compressor, and the C3 refrigerant compressor are matched to one another in terms of their torque.

14. The plant according to claim 13, which is operated without using a high-pressure steam boiler.

15. The plant according to claim 13, further comprising at least four frequency converters, each frequency converter being provided as part of a frequency converter arrangement, wherein:
   two or four frequency converters are used at any time to feed the electric drives;
   a frequency converter arrangement is held in an operational state while the plant produces ethylene and/or other olefins by steam cracking; and
   each frequency converter arrangement comprises an input transformer and an input and output, wherein the input and output are connected via switching units to a current source and a respective drive.

16. The plant according to claim 13, wherein the crude gas compressor is configured to carry out an intermediate cooling at least temporarily using external refrigeration.

17. The method according to claim 9, wherein the intermediate cooling is then carried out using external refrigeration when a cooling water temperature and/or water injection is recognized as being insufficient and/or not functional.

18. The method according to claim 1, which is operated without using a high-pressure steam boiler.

* * * * *